United States Patent [19]
Samsel et al.

[11] Patent Number: 5,447,465
[45] Date of Patent: Sep. 5, 1995

[54] METHOD OF TREATING NEEDLE BLANKS

[75] Inventors: Scott Samsel, Bristol; Marcellino Munoz, Waterbury, both of Conn.

[73] Assignee: United States Surgical Corporation, Norwalk, Conn.

[21] Appl. No.: 91,545

[22] Filed: Aug. 19, 1993

[51] Int. Cl.⁶ .............................................. B24B 31/00
[52] U.S. Cl. ...................................... 451/32; 451/326
[58] Field of Search .................. 51/6, 7, 163.1, 163.2, 51/164.1, 164.2, 164.5, 313, 315, 316; 451/32

[56] References Cited

U.S. PATENT DOCUMENTS

| | | |
|---|---|---|
| 389,552 | 9/1888 | Dean . |
| 722,105 | 3/1903 | Hervey . |
| 957,999 | 5/1910 | Parsons . |
| 1,352,598 | 9/1920 | Hart . |
| 1,750,499 | 3/1930 | Truax . |
| 2,062,671 | 12/1936 | Lupo, Jr. . |
| 2,174,880 | 10/1939 | Hilbish et al. . |
| 2,185,262 | 1/1940 | Lupo, Jr. . |
| 2,318,578 | 5/1943 | Balz et al. . |
| 2,318,579 | 5/1943 | Balz et al. . |
| 2,318,580 | 5/1943 | Balz et al. . |
| 2,435,488 | 2/1948 | Baylin ............................ 51/164.1 |
| 2,439,156 | 4/1948 | Castle . |
| 2,440,656 | 4/1948 | Huntington . |
| 2,545,291 | 3/1951 | Lupo .............................. 51/164.5 |
| 2,978,850 | 4/1961 | Gleszer . |
| 2,994,165 | 8/1961 | Brevik . |
| 3,022,017 | 2/1962 | McKenna . |
| 3,100,088 | 8/1963 | Podmore et al. . |
| 3,230,671 | 1/1966 | Rampe . |
| 3,239,970 | 3/1966 | Bishop . |
| 3,394,704 | 7/1968 | Dery . |
| 3,453,782 | 7/1969 | Hageluken et al. . |
| 3,589,428 | 6/1971 | Masujima . |
| 3,680,266 | 8/1972 | Shiplov . |
| 3,702,758 | 11/1972 | Fukui et al. ............................ 51/298 |
| 3,788,119 | 1/1974 | Arrigo . |
| 3,997,358 | 12/1976 | Taylor . |
| 3,998,259 | 12/1976 | Zocher . |
| 4,044,814 | 8/1977 | Zocher . |
| 4,054,144 | 10/1977 | Hoffman et al. . |
| 4,072,041 | 2/1978 | Hoffman et al. . |
| 4,127,219 | 11/1978 | Mabus . |
| 4,258,505 | 3/1981 | Scheiber et al. . |
| 4,430,358 | 2/1984 | Wada ............................. 51/227 H |
| 4,455,858 | 6/1984 | Hettich . |
| 4,524,815 | 6/1985 | Pavel et al. . |
| 4,541,470 | 9/1985 | Pavel . |
| 4,548,251 | 10/1985 | Lange . |
| 4,561,445 | 12/1985 | Berke et al. . |
| 4,785,868 | 11/1988 | Koenig, Jr. . |
| 4,978,259 | 12/1990 | Wollam . |
| 5,042,558 | 8/1991 | Hussey et al. . |
| 5,139,514 | 8/1992 | Korthoff et al. . |
| 5,140,783 | 8/1992 | Hoffman . |
| 5,295,330 | 3/1994 | Hoffman . |

OTHER PUBLICATIONS

Oakite Material Safety Data Sheet (Dated Oct. 25, 1990).

Dreher *Precision Sliding Grinding In Centrifugal Equipment* (Industrial & Production Engineering, 1985).

*Primary Examiner*—Jack W. Lavinder

[57] ABSTRACT

A process for tumbling needle blanks either before or after suture holes have been drilled into the respective needle blanks preferably tumbling occurs with smooth, e.g. ceramic or glass spherical media, or soft media.

15 Claims, 1 Drawing Sheet

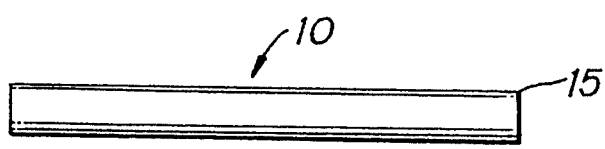
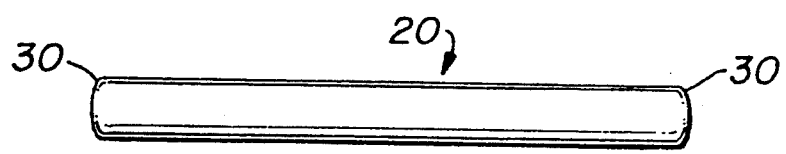
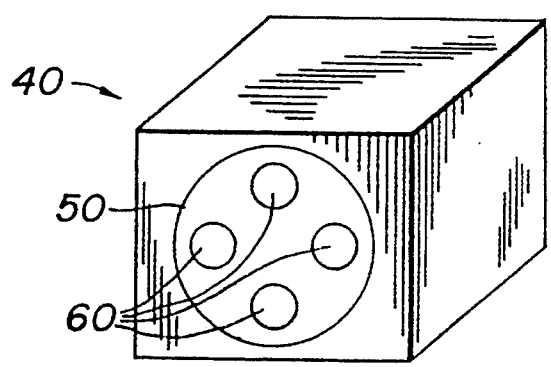

METHOD OF TREATING NEEDLE BLANKS

BACKGROUND OF INVENTION

1. Field of Invention

The present invention relates to a method of mechanically treating needle blanks used for fabrication into surgical needles, and more particularly to a method for deburring and chamfering said needle blanks.

2. Background of the Art

For many years, surgeons have employed needle-suture combinations in which a suture or ligature is attached to the shank end of a needle. Such needle-suture combinations are provided for a wide variety of monofilament and braided suture materials, both absorbable and nonabsorbable, e.g., catgut, silk, nylon, polyester, polypropylene, linen, cotton, and absorbable synthetic materials such as polymers and copolymers of glycolic and lactic acids.

Needle-suture combinations fall into two general classes: standard needle attachment and removable or detachable needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture (for various suture sizes) are set forth in the United States Pharmacopoeia (USP). The United States Pharmacopoeia prescribes minimum individual pull-out forces as measured for five needle-suture combinations. The minimum pull-out forces for both standard and removable needle-suture attachment set forth in the United States Pharmacopoeia are hereby incorporated by reference.

On typical method for securing a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out value of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031) and pretensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and 4,127,133.

To fabricate a surgical needle, needle blanks are cut by conventional cutting means from wire stock. For those needle-suture combinations wherein the suture is inserted into a longitudinal cylindrical recess in the barrel end of the needle, one end of the needle blank is drilled by mechanical or laser means.

The cutting and drilling produces burrs, and, in the case of laser drilling, burn spots which must be removed. Also, the cutting process leaves a sharp, circumferential periphery at the butt end. If the sharp edge is not removed there is a possibility that a suture connected to the needle might be cut or damaged by coming into contact with the edge. This can occur, for example, if the suture is bent sharply around in the vicinity of the needle end.

Needle blanks, therefore, are subjected to mechanical treating to deburr and chamfer the needle blank.

Deburring and chamfering can be accomplished by any one of several machining techniques such as grinding, lathing, and tumbling.

Tumbling is a preferred method for deburring and chamfering because of its convenience. The needle blanks are placed in a drum with abrasive particles, e.g. and agitated by rotation of the drum. However, these abrasive particles, e.g., aluminum oxide, silicon oxide, zinc oxide, dull the surface. The abrasion, while deburring and chamfering the needle blank, also scratches the needle surface, thereby requiring a subsequent polishing step to renew the fine finish of the needle. Elimination of the extra polishing step would reduce the time and cost required to make a surgical needle.

SUMMARY OF THE INVENTION

Accordingly, a method for tumbling needle blanks is provided herein to deburr and chamfer the needle blanks without requiring a subsequent polishing step. The method includes placing the needle blanks in a tumbler with a non-abrasive medium comprising particles having a surface smoothness sufficient to avoid scratching the needle blanks. The media may be substantially spherical. However, non-spherical media, e.g. stainless steel tapered pins, may also be employed. The media is generally smooth. If the media is rough, it should be softer than the blanks.

BRIEF DESCRIPTION OF THE DRAWINGS

FIG. 1 shows a needle blank prior to tumbling;

FIG. 2 shows an end of the needle blank of FIG. 1;

FIG. 3 shows a needle blank after tumbling according to the present invention;

FIG. 4 shows an end of the needle blank of FIG. 3; and

FIG. 5 shows a typical tumbling apparatus.

DETAILED DESCRIPTION OF PREFERRED EMBODIMENTS

The needle blanks to be treated by the tumbling operation of the present invention may be fabricated from any material suitable for the manufacture of surgical needles. Such material may be, for example, an alloy of stainless steel.

The alloy is originally in the form of wire stock which is straightened (if necessary) and cut into needle blanks by processes and machinery familiar to those with skill in the art. The needle blanks typically have a diameter of from about 1.5 mils for ophthalmic needles to about 62 mils for sternum needles. A mil is one thousandth of an inch. The needle blanks may be drilled at one end, either mechanically or by laser drilling, to form an axially aligned hole therein for the reception of a surgical suture.

The needle blank needs to be chamfered, deburred, ground to a sharp point and polished. Chamfering, deburring and polishing are accomplished herein by a tumbling operation wherein the needle blanks are placed in a tumbler with particles of tumbling medium.

The particles of tumbling media must be able to deburr and/or chamfer the needle blanks without causing scratching of the needle surface. To accomplish this the tumbling medium must either have a hardness less than or equal to that of the needle blanks (i.e. a "soft" medium), or the particles of tumbling medium must have a smooth surface, i.e. no sharp points or edges capable of causing a visible scratch. A suitable "hard" medium (i.e. one having a hardness greater than that of the needle blanks) comprises particles having no curved surface feature with a radius less than the diameter of the needle blank. The media may be substantially spherical. However, non-spherical media, e.g. stainless steel tapered pins, may also be employed. The media is generally smooth. If the media is rough, it should be softer than the blanks.

The particles of hard media are preferably spherical and have a diameter of from about 0.5 millimeters (mm) to about 10 mm, preferably about 2 mm to about 7 mm and a glassy smooth surface. The diameter varies with the size of the needle blank. For large (18–30 mil) wire diameters a spherical particle diameter of about 4 to about 8 mm is preferred. For small (down to 10 mil) wire diameters a spherical particle diameter of about 1 to about 3 mm is preferable. Hard media suitable for tumbling in the present invention include, for example, ceramic, porcelain, stainless steel and glass.

Porcelain is a non-abrasive ceramic. Most preferably the media is spherical porcelain.

The present invention has the advantage that it can deburr without losing the clarity and shine of the needles.

FIGS. 1 and 3 show a typical needle blank end before (blank 10) and after (blank 20) deburring, respectively. The deburring radiuses the sharp edges 15 of the needle blank end 10. This results in radiused edges 30. This helps prevent the edges from nicking and cutting a suture (not shown) during use.

A typical small ceramic media is Daistone DP-1 two (2)mm media made by Nippon Dia Industry Co., Ltd., 7-26, 3-Chome, Nishi-shinjuku, Shinjuku-ku, Tokyo, Japan. A typical large ceramic media is VF-P, six (6)mm media made by Vibra Finish Co., 8491 Seward Road, Hamilton, Ohio 45011.

Metallic media is generally used for larger needles in the disclosed needle size range. Such metallic media could bend relatively smaller needles.

Because of the extreme weight differences of standard metallic media relative to needles, glass or porcelain media is preferred. Porcelain is most preferred because it is generally more durable than glass.

The media provides a burnishing surface which is free of abrasive surfaces. Thus, deburring occurs by peening rather than abrasion. The tumbling of the present invention maintains the polish of the needles. This has the major advantage of deburring without a need for repolishing the needles after deburring.

Tumbling with the above media may be performed in a wet or dry (preferably wet) fashion. Low liquid, e.g. water, levels are harsher than high liquid levels. In wet tumbling, an acidic or basic agent is present with the media during tumbling. A typical alkaline mixture is Oakite TM FM403 made by Oakire Products, Inc., 50 Valley Road, Berkeley Heights, N.J. 07922. Such a mixture gives lubricity and helps clean parts. An acidic or alkaline mixture may be used during tumbling of 300-type stainless steels. However, preferably an alkaline mixture is used during tumbling of 400-type stainless steels. Typically about 25 to about 75 ml. of Oakite TM (FM-403) is added per 2.5 liter barrel with the remainder being hot tap water. Also, the tumbling media and needle blanks are typically in about 0.5–2:0.5–2 volume ratio. Wet tumbling may also be performed with Dreher C-168 powder or A-13 liquid 50 cc/2.5 liter BBL along with porcelain balls to remove discolorations on wire surface.

The wet tumbling media may also have silica or lime added to it. The particle size of silica or lime is small, preferably about that of talc. Most industrial talcs have one of three general sizes: 98% minus 200-mesh screen, 98.5% minus 325-mesh screen; and 99.5% minus 325-mesh screen. Perry's Chemical Engineer's Handbook, p. 8-51, 6th Ed. McGraw-Hill (1984). Extremely fine talcs have a particle size of 5 microns and a specific area of 30 $m^2$/gm. Id.

Particles of soft, dry media can be of any shape suitable for tumbling. Thus, the media does not have to be spherical, e.g., wood pegs, triangles, or squares are suitable. Preferably the soft medium is formed into sperical particles. Because the soft medium is not harder than the needle blanks it will not cause scratching thereof. Examples of soft media include wood beads, ground walnut shell, e.g., Dreher NPG8 or NPG 1500 and ground corncob. Powders of silica or lime are generally added to the soft media to facilitate deburring. Tumbling with soft media is usually performed in a dry fashion. Liquid abrasives such as Dreher SFF may be added. Typically about 10 ml to about 50 ml of liquid abrasive are added per 2.5 liter barrel. Alternatively, 1–5 tsp./2.5 liter BBL of dry abrasives such as Dreher TPP may be added.

Either centrifugal or vibratory tumbling may be employed. During centrifugal tumbling, the tumbler may be rotated about a horizontal axis. Alternatively the tumbler can agitate the needle blanks and media by means of rotation around a vertical axis.

FIG. 5 schematically shows a centrifugal tumbler 40 having a drum 50. Within the drum are four chambers 60. The drum 50 turns counterclockwise while the chambers 60 turn clockwise. Such a tumbler may create up to 25 gravities of force in its chambers. The typical duration of centrifugal tumbling ranges from ten (10) minutes to one (1) hour. Additional background on centrifugal tumbling is provided by Dreher et al., Precision Sliding Grinding in Centrifugal Equipment, Industrial and Production Eng., Vol. 2 (1985), incorporated by reference. An example of a centrifugal tumbler is made by Dreher Corp., 57 George Leven Drive, Attleboro, Mass. 02703. This address is that of Dreher's U.S. Distributor. The parent of Dreher Corp. is a German company.

Centrifugal tumbling is faster than vibratory tumbling. However, vibratory tumbling is gentler. The typical duration of vibratory tumbling is one (1) hour to sixteen (16) hours. A typical vibratory tumbler is made by Ray Tech, P.O. Box 6, Route 32, Stafford Industrial Park, Stafford Springs, Conn. 06076 under the designations TUMBLE-VIBE and ADJUSTA-VIBE.

Example 1

Load a 2.5 liter volume barrel of a centrifugal tumbler by placing one layer of white porcelain beads and one layer of needle blanks to be tumbled. Cover beads lightly to have a volume ratio of 5 parts media to part needle blanks. Repeat layering steps until barrel is full. Add about 50 to 100 ml. of Oakite TM FM-403 and fill barrel with hot tap water. Repeat the above steps for up to three additional barrels. The barrels should be balanced. If only one barrel of parts is to be tumbled then load the barrel opposite the full barrel with beads, water and soap. If three barrels are to be tumbled then load the fourth barrel with beads, water and soap. For straightened and cut blanks, tumble for 45-60 minutes at about 250 rpm. For drilled blanks tumble for 5-10 minutes at about 250 rpm. After tumbling one would remove the barrels from the tumbling machine and empty the barrel contents. Then one would rinse the barrel contents under hot tap water and separate tumbled parts from beads.

Example 2

Cut and straightened needle blanks are loaded into a vibratory tumbler (e.g. Adjusta-Vibe TM tumbler of Raytech having a 0.25 cubic foot volume along with 10-100 milliliters of OAKITE TM FM-403 solution and about three cups (24 oz.) of hot water. Fill tumbler three fourths with white porcelain beads. Place cover on tumbler and tumble parts for about two (2) hours. Rinse tumbled parts with hot water and separate beads from needle blanks. It is understood that the present invention is not limited by the present specification but it is defined by the claims appended hereto.

We claim:

1. A process for deburring and reducing sharp edges of needle blanks comprising the step of:
    tumbling said needle blanks with spherical media having a smooth surface and a hardness greater than the hardness of the needle blanks for sufficient time to deburr said needle blanks, wherein the spherical media have a particle diameter of about 4 mm to about 8 mm and the needle blanks have a diameter of from about 18 to about 30 mils.

2. The process of claim 1, wherein said spherical media comprises porcelain.

3. The process of claim 1, wherein said spherical media comprises glass.

4. A process for deburring and reducing sharp edges of needle blanks comprising the step of:
    tumbling said needle blanks with spherical media having a smooth surface and a hardness greater than the hardness of the needle blanks for sufficient time to deburr said needle blanks, wherein the spherical media have a particle diameter of about 1 to about 3 mm and the needle blanks have a diameter from about 17 to about 10 mils.

5. A process deburring and reducing sharp edges of polished needle blanks comprising the steps of:
    tumbling said needle blanks with media having a hardness less than or equal to the hardness of the needle blanks for sufficient time to deburr said needle blanks, wherein said media comprises wood, walnut shells or ground corn cob, said media further comprising a powder of silica or lime, wherein the powder has a particle diameter such that at least 98% of the particles are less than 200 mesh.

6. The process of claim 5, wherein said wood, walnut, or ground corn cob media has a diameter of from about 0.5 millimeters to about 10 millimeters.

7. The process of claim 5, wherein the wood, walnut, or corn cob media has a particle diameter of about 1 to about 3 mm and the needle blanks have a diameter from about 17 to about 10 millimeters.

8. The process of claim 5, wherein an abrasive liquid is added to the media to be present during said tumbling.

9. A process for deburring and reducing sharp edges of polished needle bands comprising:
    tumbling said needle blanks with media having a smooth surface for sufficient time to deburr said needle blanks and simultaneously retain the polish of said needle blanks, wherein the media have a particle diameter of from about 4 mm to about 8 mm and the needle blanks have a diameter of from about 18 to about 30 mils.

10. A process for deburring and reducing sharp edges of polished needle blanks comprising:
    tumbling said needle blanks with media having a smooth surface for sufficient time to deburr said needle blanks and simultaneously retain the polish of said needle blanks, wherein the media have a particle diameter of from about 1 mm to about 3 mm and the needle blanks have a diameter of from about 17 mils to about 10 mils.

11. A process for deburring and reducing sharp edges of polished needle blanks comprising:
    tumbling said needle blanks with media having a surface softer than the needle blanks for a sufficient time to deburr said needle blanks and simultaneously retain the polish of said needle blanks, wherein aid media comprises a material selected from the group consisting of wood, walnut shell, and ground corn cobs, and wherein said media further comprises a powder selected from the group consisting of silica and lime, wherein the powder has a particle diameter of such that at least 98% of the particles are less than 200 mesh.

12. The process of claim 11 wherein the media has a particle diameter of about 1 mm to about 3 mm and the needle blanks have a diameter of from about 17 mils to about 10 mils.

13. The process of claim 11 wherein an abrasive liquid is added to the media to be present during tumbling.

14. A process for deburring and reducing sharp edges of polished needle blanks, comprising:
    tumbling said needle blanks with a media having a smooth surface with no curved surface feature having a radius less than a diameter of the needle blanks and a hardness greater than the hardness of the needle blanks.

15. The process of claim 14 wherein the diameter of the needle blanks ranges from about 10 mils to about 30 mils.

* * * * *